United States Patent
McNeirney et al.

(10) Patent No.: US 7,603,163 B2
(45) Date of Patent: *Oct. 13, 2009

(54) TARGETING SYSTEM AND METHOD OF TARGETING

(75) Inventors: John C. McNeirney, Fairburn, GA (US); Peter Solender, Williamsville, NY (US); Haibo Wang, North Tonawanda, NY (US)

(73) Assignee: Minrad Inc., Orchard Park, NY (US)

( * ) Notice: Subject to any disclaimer, the term of this patent is extended or adjusted under 35 U.S.C. 154(b) by 558 days.

This patent is subject to a terminal disclaimer.

(21) Appl. No.: 10/977,759

(22) Filed: Oct. 29, 2004

(65) Prior Publication Data

US 2005/0169434 A1 Aug. 4, 2005

Related U.S. Application Data

(60) Provisional application No. 60/516,039, filed on Oct. 31, 2003.

(51) Int. Cl.
*A61B 6/00* (2006.01)
(52) U.S. Cl. .................. 600/426; 600/424; 600/427; 600/407; 378/205; 378/206
(58) Field of Classification Search .......... 600/426, 600/407, 427; 378/65, 206, 205, 20; 606/130; 356/399; 250/398
See application file for complete search history.

(56) References Cited

U.S. PATENT DOCUMENTS

| 4,836,671 | A | * | 6/1989 | Bautista ............. 356/3.1 |
| 5,644,616 | A | * | 7/1997 | Landi et al. ......... 378/206 |
| 6,104,779 | A | * | 8/2000 | Shepherd et al. ..... 378/65 |
| 6,694,169 | B2 | * | 2/2004 | Kennedy et al. ...... 600/426 |

* cited by examiner

*Primary Examiner*—Brian L. Casler
*Assistant Examiner*—John F Ramirez
(74) *Attorney, Agent, or Firm*—Hodgson Russ LLP

(57) ABSTRACT

A targeting system, which provides an adjustable optical assembly, for use with imaging systems having a penetrating beam source, a penetrating beam receiver. The optical assembly has a targeting marker in the path of a penetrating beam emitted by the source. The targeting marker is at least partially opaque to the penetrating beam emitted by the source, and the targeting marker indicates a targeting point on a target axis. The optical assembly further includes a sensible targeting beam device that is capable of providing a sensible targeting beam coaxial and collinear with the target axis. In addition, there is provide a method of aligning the targeting system, such as the system described above, and a method of targeting an area of interest. One advantage of the system and method is that it requires only a two point alignment.

36 Claims, 7 Drawing Sheets

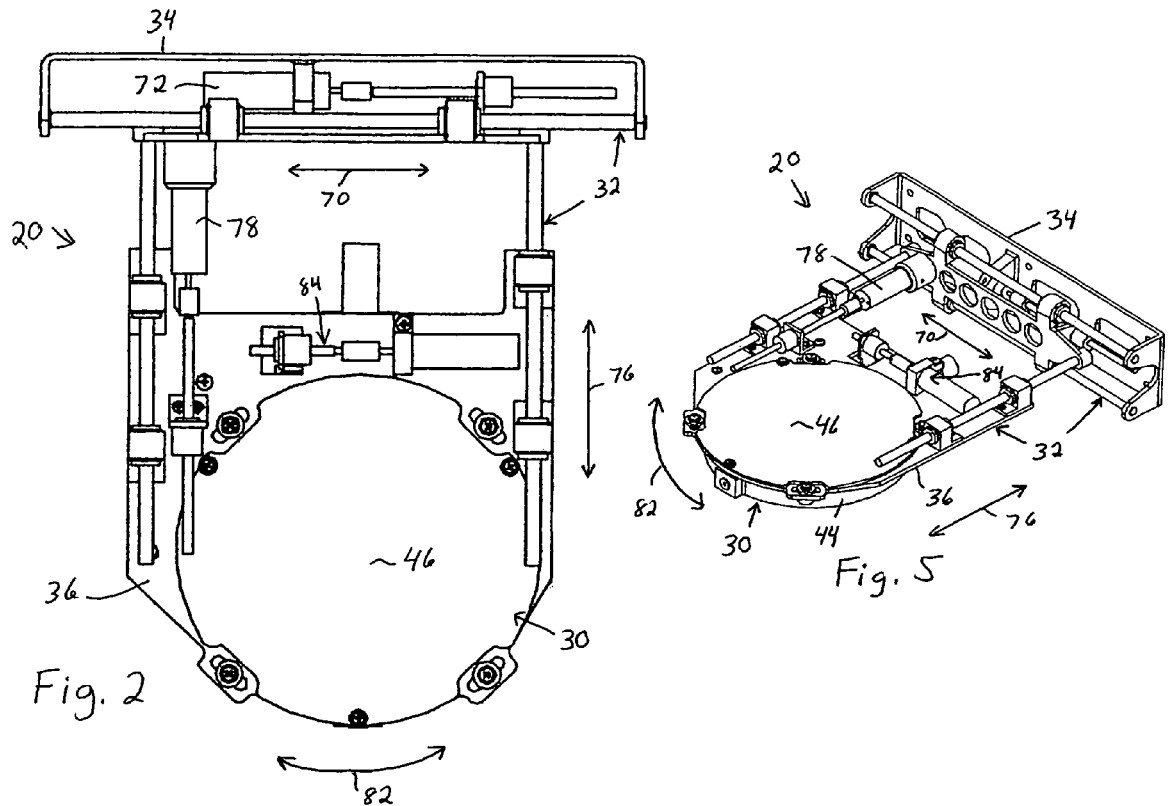
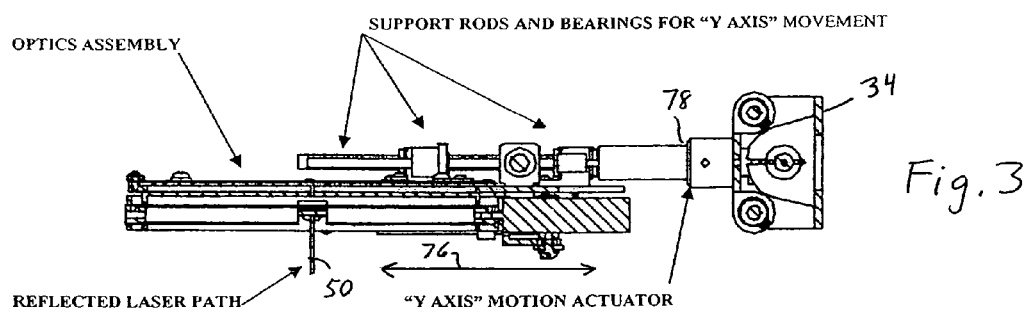
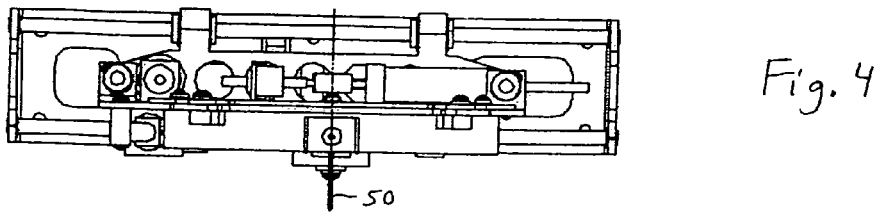

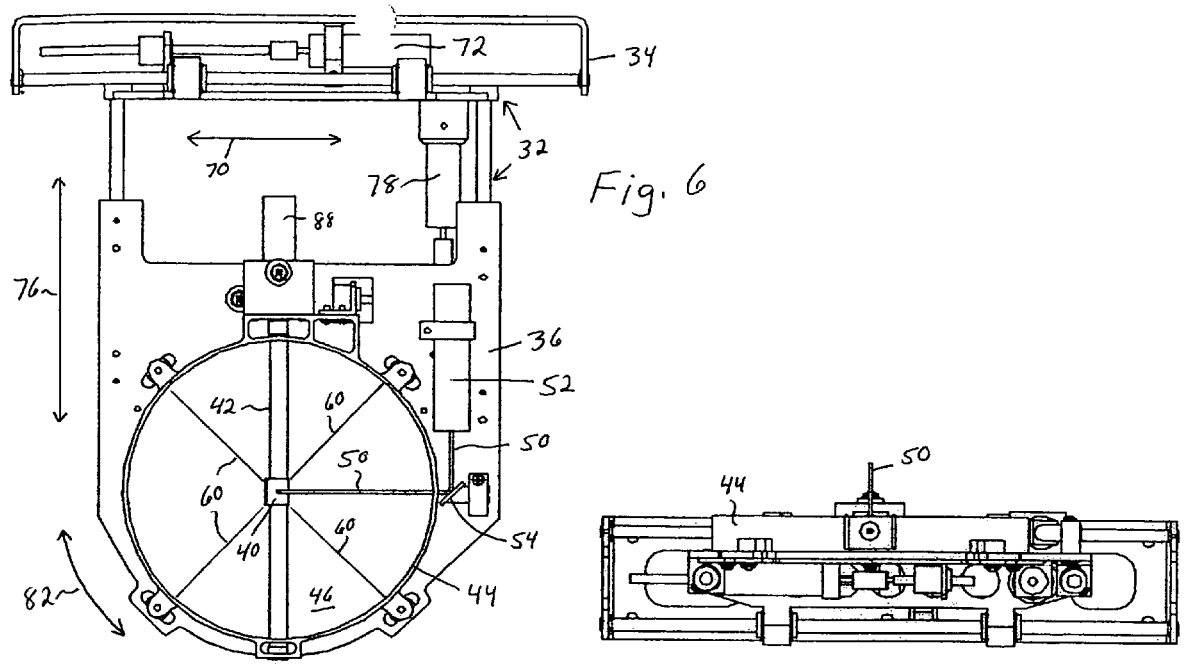
Fig. 6
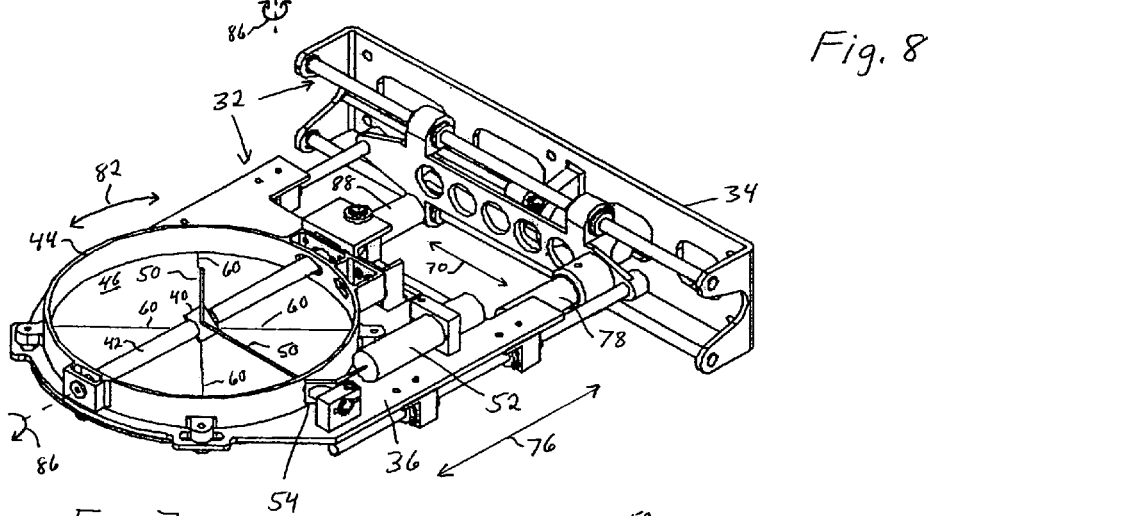
Fig. 8
Fig. 7
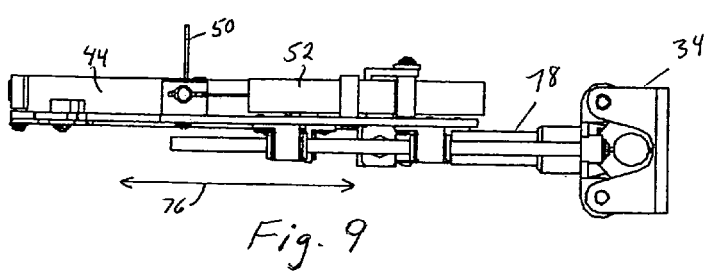
Fig. 9

TARGETING SYSTEM AND METHOD OF TARGETING

CROSS REFERENCE TO A RELATED APPLICATION

Applicants claim priority based on U.S. provisional patent application No. 60/516,039 filed Oct. 31, 2003 and entitled "Targeting System And Method of Targeting," the disclosure of which is incorporated by reference.

BACKGROUND OF THE INVENTION

The present invention relates generally to systems and methods of targeting. For example, the present invention may be used to target areas residing behind a surface.

In the prior art, U.S. Pat. No. 5,320,111 and U.S. Pat. No. 5,316,014 disclose a method and apparatus for locating and guiding a biopsy needle with respect to an X-rayed specimen having a tumor to be engaged by the needle. Intersecting laser beams are utilized to mark the location of the tumor and to guide the biopsy needle in a vertical path. The laser beam source is movable in orthogonal paths while compensating means redirect the beams to maintain them within a target area or eliminate any parallax. That is, the angular position of the laser light beam is adjusted to different angles at different coordinate positions to have the needle follow along a portion of a straight line path from the X-ray point source through the lesion and to the X-ray film. Thus, the needle tip should not be displaced to one side of a small lesion.

Such prior art systems and methods have disadvantages. For instance, they are difficult to accurately and quickly calibrate. An improved targeting system and method of targeting is disclosed in pending U.S. patent application Ser. No. 09/792,191 filed Feb. 22, 2001 entitled "Targeting System And Method Of Targeting" and assigned to the assignee of the present invention, the disclosure of which is hereby incorporated by reference.

SUMMARY OF THE INVENTION

The present invention includes a targeting system, which provides an adjustable optical assembly, for use with imaging systems having a penetrating beam source, a penetrating beam receiver. The optical assembly has a targeting marker in the path of a penetrating beam emitted by the source. The targeting marker is at least partially opaque to the penetrating beam emitted by the source, and the targeting marker indicates a targeting point on a target axis. The optical assembly further includes a sensible targeting beam device that is capable of providing a sensible targeting beam coaxial and collinear with the target axis.

In addition, the present invention includes a method of aligning the targeting system, such as the system described above, and a method of targeting an area of interest.

One advantage of the system and method of the present invention is that it requires only a two point alignment.

BRIEF DESCRIPTION OF THE DRAWINGS

For a fuller understanding of the nature and objects of the invention, reference should be made to the following detailed description taken in conjunction with the accompanying drawings, in which:

FIG. 2 is a plan view of the targeting assembly included in the system of FIG. 1;

FIG. 3 is a side elevational view of the targeting assembly of FIG. 2;

FIG. 4 is an end elevational view of the targeting assembly of FIG. 2;

FIG. 5 is a perspective view, reduced in size, of the targeting assembly of FIG. 2;

FIG. 6 is an opposite plan view of the targeting assembly included in the system of FIG. 1;

FIG. 7 is a perspective view of the targeting assembly of FIG. 6;

FIG. 8 is an end elevational view of the targeting assembly of FIG. 6;

FIG. 9 is a side elevational view of the targeting assembly of FIG. 6;

DETAILED DESCRIPTION OF THE INVENTION

The targeting system is used in conjunction with a real-time imaging system. The imaging system may be a fluoroscopic X-ray imaging system, a film (or equivalent recording media) X-ray imaging system, a NMR (nuclear magnetic resonance also known as MRI) imaging system, a CAT (computer assisted tomography also known as CT) imaging system. All of the aforementioned imaging systems have a source of penetrating electromagnetic radiation beam and a device which receives and interprets the resulting penetrating radiation image. The targeting system may also be used with systems using other forms of penetrating radiation such as ultrasound radiation. The targeting system may be in an embodiment that is attachable to an existing image system or in an embodiment which can be included into the imaging system.

By way of background, reference may be made to FIG. 4 of the above-referenced application Ser. No. 09/792,191 which is a schematic perspective view of part of a targeting assembly which is included in a targeting system. That targeting assembly is a three point alignment system for use with the C-arm shown in that application for mapping the shape of the conical X-ray beam. That targeting assembly features pivotal movement about axis 25C shown in FIG. 4 of application Ser. No. 09/792,191, reciprocating movement along axis 25A and along axis 25C and pivotal movement about axis 25A.

The embodiment of the targeting system of the present invention includes an optical assembly, the associated motion actuators, the associated electronic elements and other associated operational control devices such as, but not limited to, an infrared based remote controller. The optical assembly is adjustable. The optical assembly has a targeting marker in a path of a penetrating beam provided by the radiation source. The targeting marker is at least partially opaque to the penetrating beam emitted by the radiation source, and the targeting marker indicates a targeting point on a target axis. The optical assembly further includes a sensible targeting beam device capable of providing a sensible targeting beam coaxial and coincident with the target axis. In addition, the present invention includes a method of aligning the targeting system with the particular imaging system, and a method of targeting an area of interest. One advantage of the optical assembly of the present invention is that it requires only a two point alignment.

Figure 1:
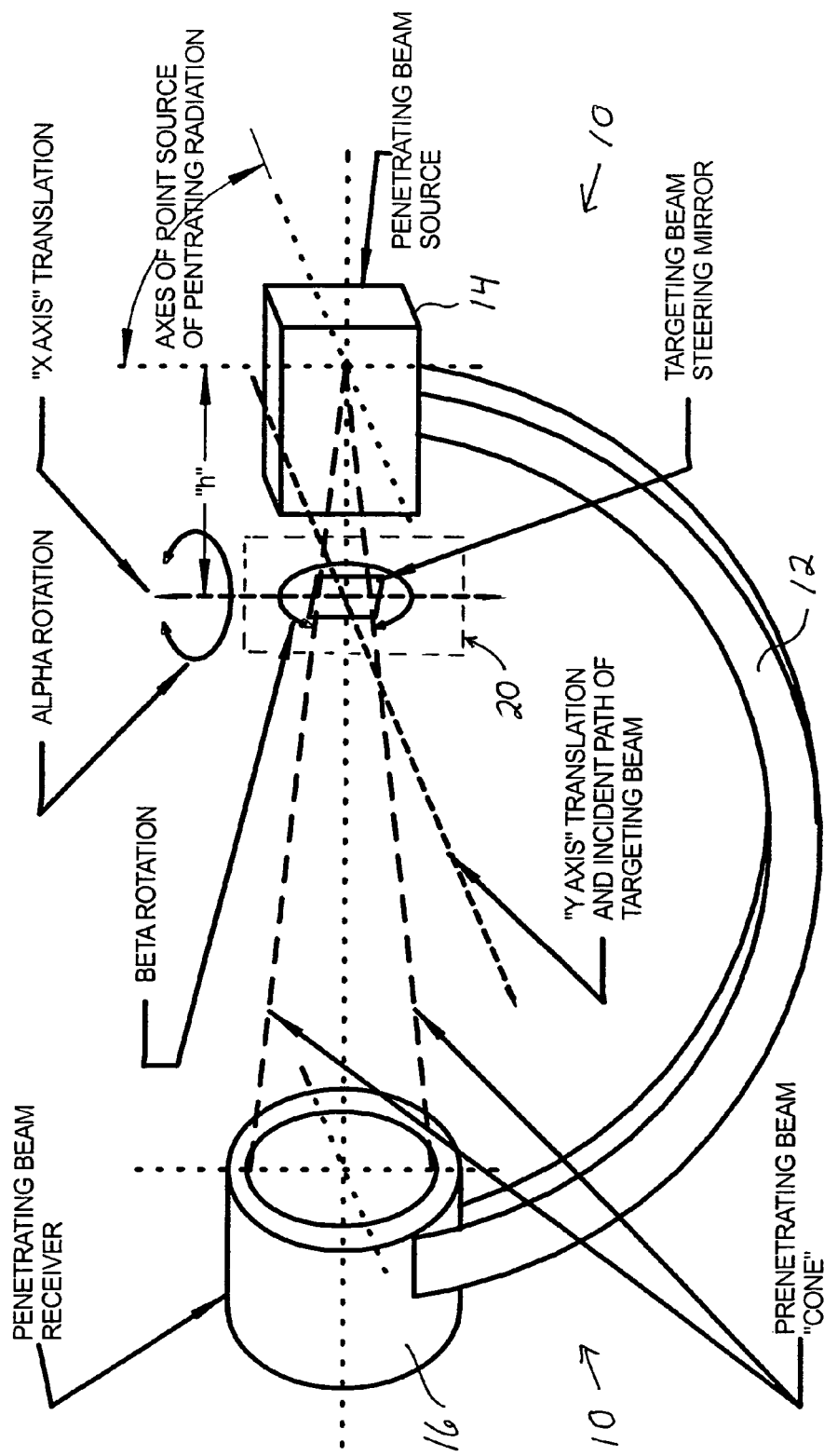
FIG. 1 is a schematic diagram of an imaging system including a targeting system according to the invention.

Referring now to FIG. 1, the targeting system of the present invention is illustrated with a fluro-scopic X-ray imaging system 10 including a c-arm 12, a penetrating beam or X-ray source 14 and a penetrating beam receiver or image intensifier 16. The targeting assembly of the invention is designated 20 in FIG. 1.

FIG. 2 is a plan view of the targeting assembly 20 looking from the source 14 toward assembly 20. FIG. 6 is a plan view of the targeting assembly 20 looking from the receiver 16 toward the assembly 20. The targeting assembly 20 comprises an optical assembly 30 carried on a frame structure 32 and various drives for moving components of the assembly in various directions as will be described. Frame 32 includes a first component 34 mounted at a fixed location in system 10 and a second component 36 carried by component 34 and which, in turn, carries optical assembly 30.

Optical assembly 30 includes a targeting beam steering mirror 40 mounted on a shaft 42 or the like rotatably mounted in a rim component 44 which, in turn, is rotatably mounted on frame component 36. A disc 46 of material allowing transmission therethrough of the penetrating beam, i.e. X-ray, is located within rim 44. A targeting beam 50, in this illustration a laser beam, is provided by a targeting beam source 52 and is directed by a cornering mirror 54 through an opening in rim 44 to the steering mirror 40. A targeting marker or reticle 60 is provided in optical assembly 30 and may be two perpendicular or orthogonal wires of X-ray opaque material extending across rim 44 in a plane parallel to the plane of disc 46.

The optical assembly 30 is moved along a first linear path in what is designated the X-axis translation in FIG. 1 and indicated by arrow 70 in FIGS. 2, 5, 6 and 7. This movement is provided by a linear actuator or the like designated 72 in FIGS. 2 and 6. The optical assembly 30 is moved along a second linear path in what is designed the Y-axis translation in FIG. 1 and indicated by arrow 76 in FIGS. 2, 3, 5, 6, 7 and 9. This movement is provided by a linear actuator or the like designated 78 in FIGS. 2, 3, 5 6, 7 and 9. The optical assembly 30 is rotated about an axis and what is designated the beta rotation in FIG. 1 and indicated by arrow 82 in FIGS. 2, 5, 6 and 7. This movement is provided by the drive arrangement designated 84 in FIGS. 2 and 5 which can comprise, for example, a stepper motor and gear arrangement. The component 42 on which steering mirror 40 is mounted is rotated about an axis and what is designated the alpha rotation in FIG. 1 and indicated by arrow 86 in FIGS. 6 and 7. This movement is provided by the drive designated 88 in FIGS. 6 and 7.

The present invention is illustrated by the following description of the operational geometry and calibration. For purposes of the following description, the distance h is defined in FIG. 1, the laser-mirror incident point is on steering mirror 40, the reticle is the targeting marker 60, and the mirror-cross-laser set is the mirror 40, reticle 60 and laser set.

Geometry for the Saber Source with Known h' (2 Point Calibration):

1. Operational geometry.
2. Calibration

Annotation:

| | |
|---|---|
| $\Delta_x, \Delta_y, \Delta_\alpha, \Delta_\beta$ | Linear and rotational step size |
| $n_x, n_y, n_\alpha, n_\beta$ | Number of steps |
| $\Delta x = n_x \Delta_x, \Delta y = n_y \Delta_y,$ | Coordinate for computation |
| $\alpha = n_\alpha \Delta_\alpha, \beta = 45° + n_\beta \Delta_\beta$ | |
| $x_0, y_0$ | System offset |
| $x = x_0 + \Delta x, y = y_0 + \Delta y$ | Assistant coordinate (intermediate) |

1. Operational Geometry

Considering the distance between laser-mirror incident point and the reticle.

The relation between translation of the reticle (x, y) and rotation of the mirror ($\alpha$, $\beta$) is:

$$h' = \frac{H+d}{H}h, l = \sqrt{x^2 + y^2 + h'^2}$$

$$= \sqrt{(x_0 + \Delta x)^2 + (y_0 + \Delta y)^2 + h'^2}$$

$$\alpha = \tan^{-1}\left(\frac{y}{x+l}\right) = \tan^{-1}\left(\frac{y_0 + \Delta y}{x_0 + \Delta x + l}\right) \quad (1)$$

$$\beta = \tan^{-1}\left(\frac{1}{h'}\sqrt{2l^2 + 2xl - h'^2}\right) \quad (2)$$

$$= \tan^{-1}\left(\frac{1}{h'}\sqrt{2l^2 + 2(x_0 + \Delta x)l - h'^2}\right)$$

where the h is the perpendicular distance between X-ray source and the reticle.

Denote H be the height from reticle to the image intensifier, and d be the distance between laser-mirror incident point and the reticle. If the mirror is above the reticle, d is negative.

Figure 10:
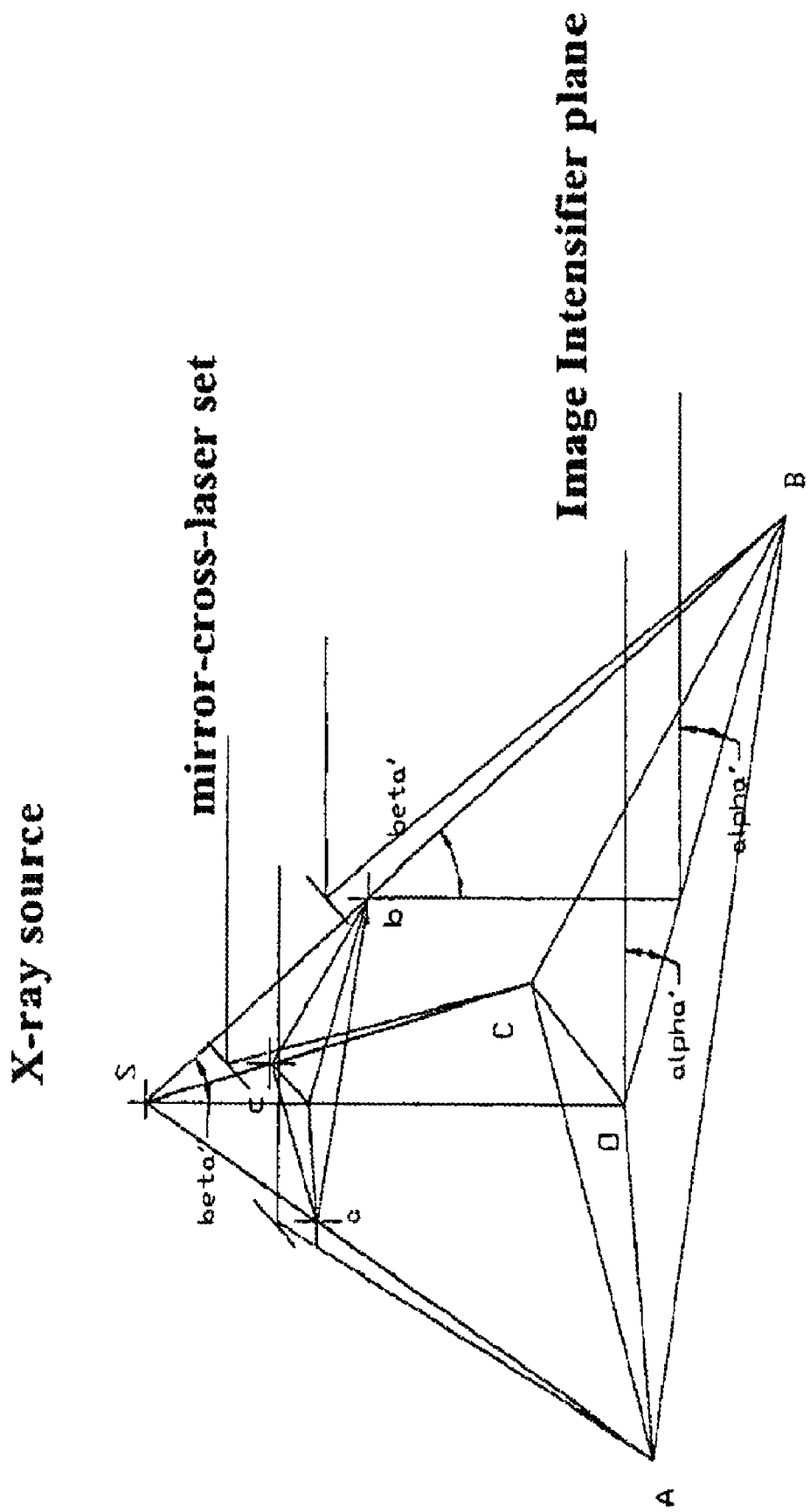
FIG. 10 depicts the geometry of the optical path of a system according to the invention showing three mirror-cross-laser set positions.

Derivation:

FIG. 10 depicts the geometry of the optical path of a system with three mirror-cross-laser set positions.

Figure 11:
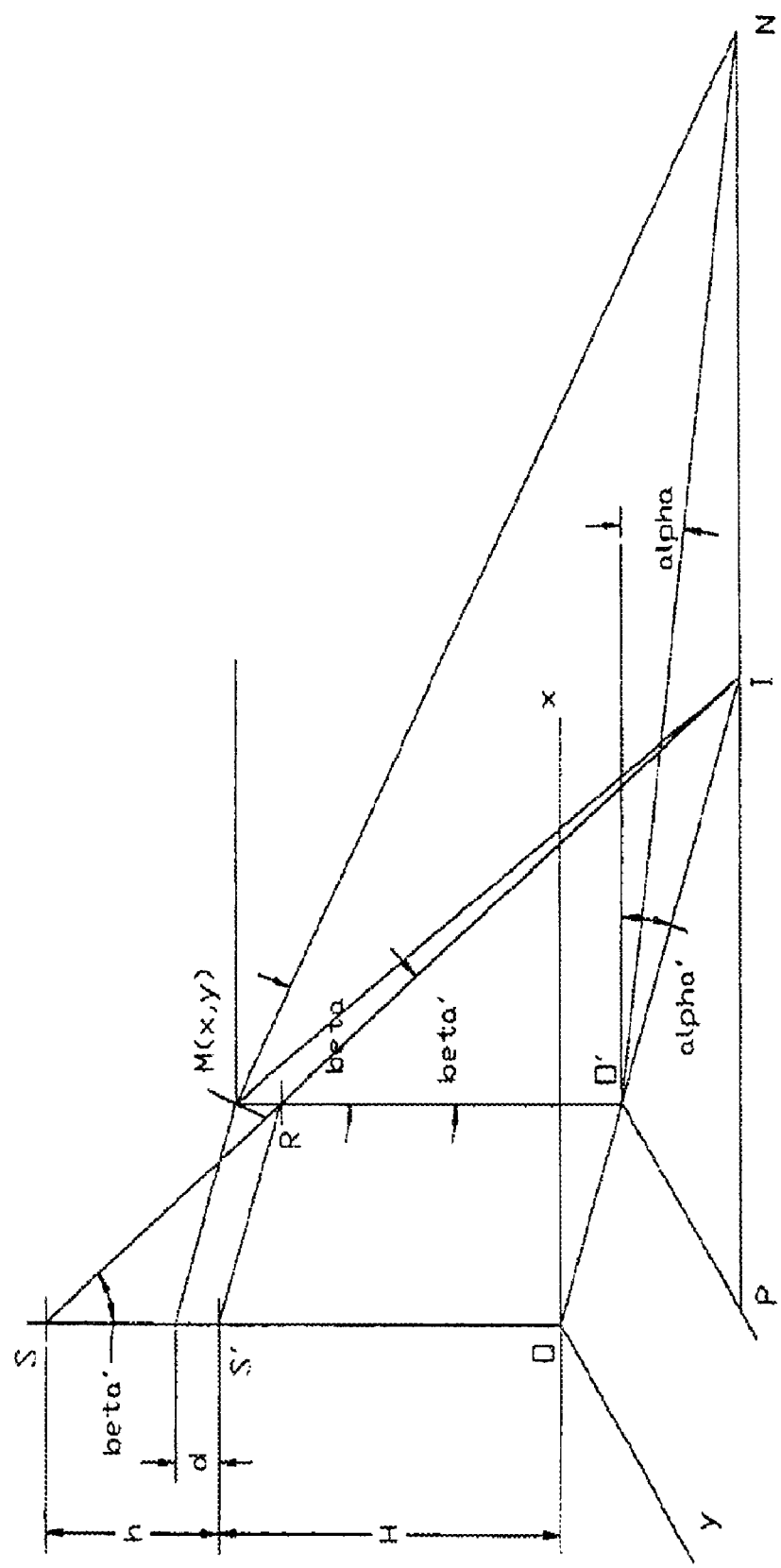
FIG. 11 depicts the geometry of a single mirror-cross-laser position.

FIG. 11 depicts the geometry of a single mirror-cross-laser position, where:

MN stands for the normal line of the mirror. The rotation of MN is expressed as $\alpha$ and $\beta$.

MI stands for the reflection ray. The rotation of MI is expressed as $\alpha'$ and $\beta'$.

R stands for the reticle.

Note: Because PIN is parallel with the laser incident ray and because MN intersect the angle between the incident ray and reflection ray, so NI=MI.

$$\tan\alpha = \frac{O'P}{PN}, \tan\beta = \frac{O'N}{H+d},$$

where:

$$MI = \sqrt{\left(\frac{H}{h}x\right)^2 + \left(\frac{H}{h}y\right)^2 + (H+d)^2}$$

$$= \frac{H}{h}\sqrt{x^2 + y^2 + \left(\frac{H+d}{H}h\right)^2} = \frac{H}{h}l$$

$$O'P = \frac{H}{h}y;$$

$$PN = PI + NI = PI + MI = \frac{H}{h}(x+l)$$

$$O'N = \sqrt{O'P^2 + PN^2}$$

-continued $$= \frac{H}{h}\sqrt{y^2 + (x+l)^2}$$

$$= \frac{H}{h}\sqrt{2x^2 + 2y^2 + h^2 + 2xl}$$

$$O'N = \sqrt{O'P^2 + PN^2}$$

$$= \frac{H}{h}\sqrt{y^2 + (x+l)^2}$$

$$= \frac{H}{h}\sqrt{2l^2 + 2xl - \left(\frac{H+d}{H}h\right)^2}$$

So $$l = \sqrt{x^2 + y^2 + \left(\frac{H+d}{H}h\right)^2}$$

$$\alpha = \tan^{-1}\left(\frac{y}{x+l}\right) \quad (1)$$

$$\beta = \tan^{-1}\left(\frac{H}{H+d} \cdot \frac{1}{h} \cdot \sqrt{2l^2 + 2xl - \left(\frac{H+d}{H}h\right)^2}\right) \quad (2)$$

2. Calibration:

Given:
  Fixed $$h' = \frac{H+d}{H}h,$$

and,
ONE translation-rotation sets of the x-y translational steps $(n_x, n_y)$ for the reticle and the rotational steps $(n_\alpha, n_\beta)$ for the mirror.

Assume: No offset at initial rotation position, i.e., $\alpha_0=0$, $\beta_0=45°$.

Find: The system offset $(x_0, y_0)$.

Conclusion:

$$y_0 = h'\tan\beta\sin\alpha - \Delta y$$

$$x_0 = \begin{cases} \sqrt{t^2 - (y_0 + \Delta y)^2 - h'^2} - \Delta x & \tan^2\beta > \tan^2\beta_0 \\ -\sqrt{t^2 - (y_0 + \Delta y)^2 - h'^2} - \Delta x & \tan^2\beta < \tan^2\beta_0 \end{cases},$$

where $t = \frac{h'(\tan^2\beta + 1)}{2\tan\beta\cos\alpha}$, and $\tan^2\beta_0 = \frac{2\cos^2\alpha - 1}{1 - 4\cos^2\alpha\sin^2\alpha}$ Or $x_0 = \pm\sqrt{t^2 - (h'\tan\beta\sin\alpha)^2 - h'^2} - \Delta x$ Note: To avoid negative numbers under the square root operation due to the computation precision, try to select calibration points with large x values (away from the y axis).

Note: Multi-point averaging may reduce calibration error.

Note:
  Make sure the laser incident ray is approximately parallel to the image intensifier.
  Have the laser incident ray be parallel to the x direction movement of the reticle.
  Have the mirror face down at the half way of β rotation initially, such that $\beta_0=45°$.
  Have the β rotational axis perpendicular to the incident laser initially such that $\alpha_0=0$.

Figure 12:
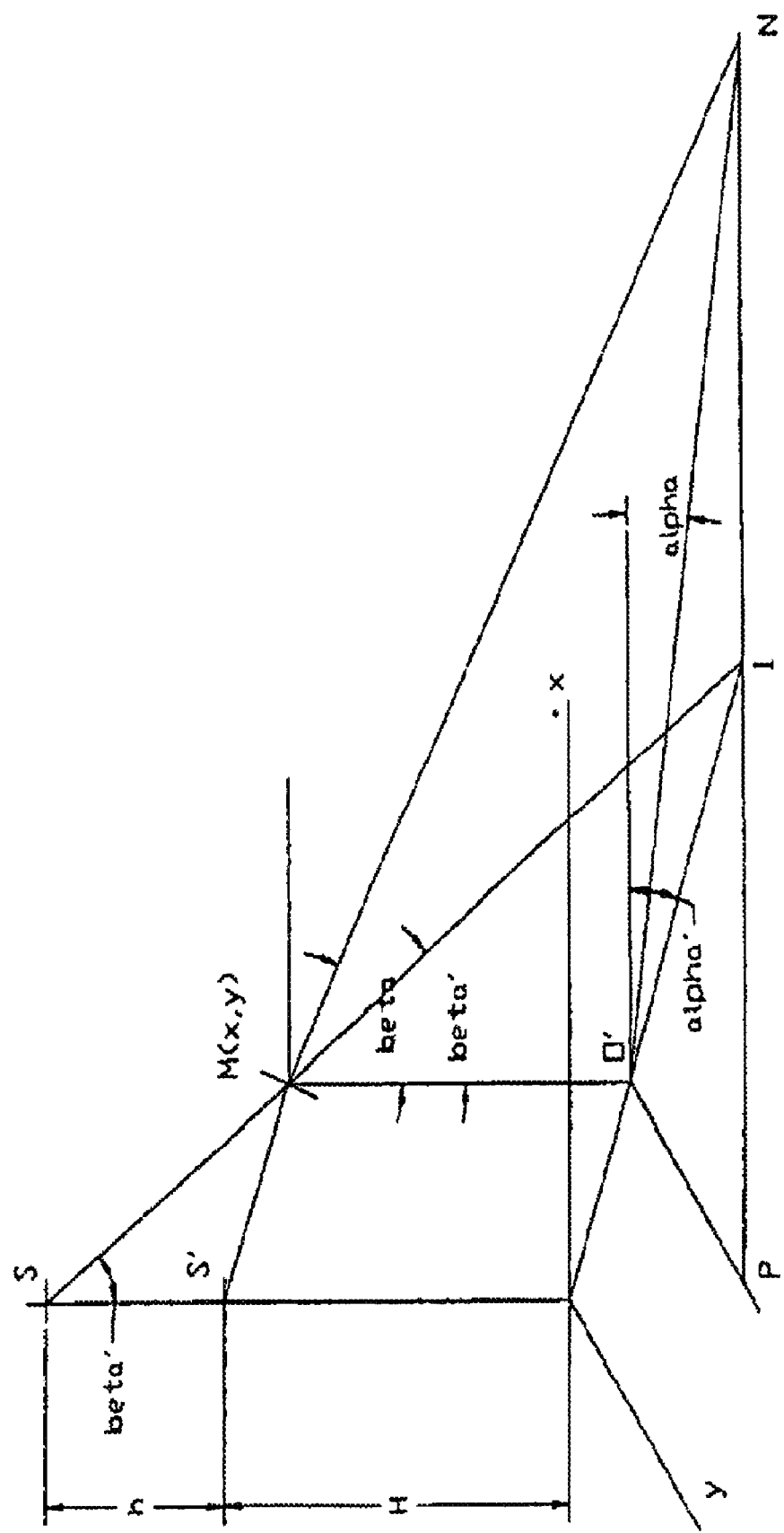
FIG. 12 depicts the geometry of an ideal case of a system.

Derivation: The geometry of an ideal case is shown in FIG. 12,

Because h is known, and $$O'P = \frac{H}{h}y = \frac{H}{h}(y_0 + \Delta y) = R\sin\alpha = H\tan\beta\sin\alpha,$$

$$\Rightarrow y_o = h\tan\beta\sin\alpha - \Delta y.$$

In addition, apply law of cosines to triangle INO', $$O'N + NI^2 - 2O'N \cdot NI\cos\alpha = O'I^2$$

where $$O'N = H\tan\beta$$

$$O'I = \frac{H}{h}\sqrt{x^2 + y^2}$$

$$NI = \frac{H}{h}\sqrt{x^2 + y^2 + h^2}$$

After simplification, $(x_0+\Delta x)^2 = t^2 - y^2 - h^2 = t^2 - (y_0+\Delta y)^2 - h^2$, where $t = \frac{h(\tan^2\beta + 1)}{2\tan\beta\cos\alpha}.$ So $$\Rightarrow x_0 = \pm\sqrt{t^2 - (y_0 + \Delta y)^2 - h^2} - \Delta x.$$

Now looking for $\beta_0$ where $x=x_0+\Delta x=0$, such that

If $\beta > \beta_0$, $x = x_0 + \Delta x > 0$, $x_0 = \sqrt{t^2 - (y_0 + \Delta y)^2 - h^2} - \Delta x$ And if $\beta < \beta_0$ $x = x_0 + \Delta x < 0$, $x_0 = -\sqrt{t^2 - (y_0 + \Delta y)^2 - h^2} - \Delta x$.

$$x = t^2 - (h'\tan\beta_0\sin\alpha)^2 - h'^2$$

$$= h'^2\left[\frac{(\tan^2\beta_0 + 1)^2}{4\tan^2\beta_0\cos^2\alpha} - \tan^2\beta_0\sin^2\alpha - 1\right] = 0$$

$$\Rightarrow \tan^4\beta_0 + 2\tan^2\beta_0 + 1 - 4\tan^4\beta_0\cos^2\alpha\sin^2\alpha - 4\tan^2\beta_0\cos^2\alpha = 0$$

$$\Rightarrow \tan^4\beta_0(1 - 4\cos^2\alpha\sin^2\alpha) + \tan^2\beta_0(2 - 4\cos^2\alpha) + 1 = 0$$

$$\Rightarrow \tan^2\beta_0 = \frac{4\cos^2\alpha - 2 \pm \sqrt{(2 - 4\cos^2\alpha)^2 - 4(1 - 4\cos^2\alpha\sin^2\alpha)}}{2(1 - 4\cos^2\alpha\sin^2\alpha)}$$

$$= \ldots = \frac{2\cos^2\alpha - 1}{1 - 4\cos^2\alpha\sin^2\alpha}$$

Figure 13:
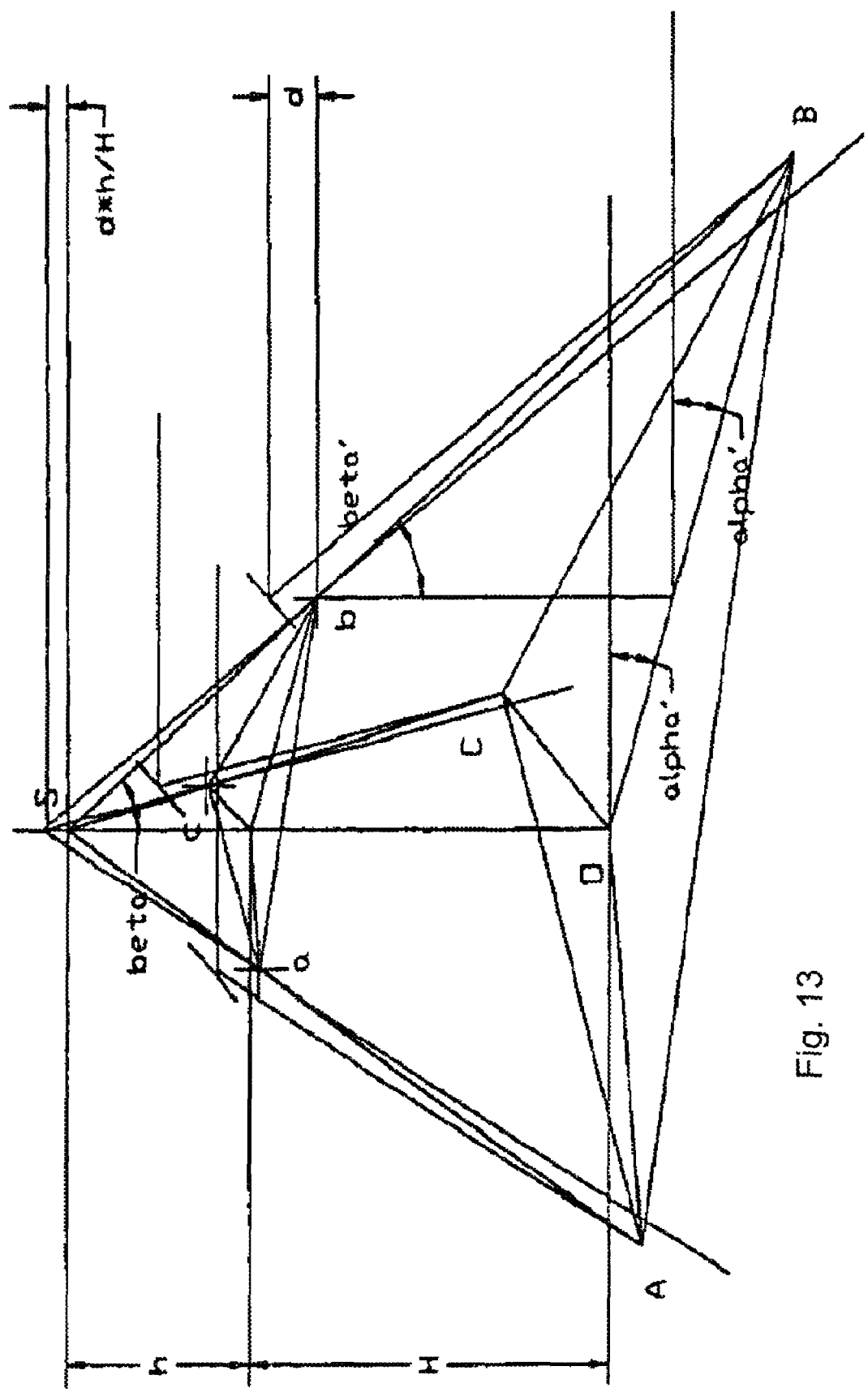
FIG. 13 depicts the geometry of a system in a non-ideal state.

When we consider the distance between laser-mirror incident point and the reticle, we will have a different h (see, e.g., FIG. 13).

FIG. 13 shows that the origin $(x_0, y_0)$ is still the same as the ideal case. However, the system height h is a little shorter than the h in the ideal case.

Let denote the new h as h'. In addition, let distance between any two calibration points on reticle plane be presented as $l_{ij}$, and the distance between two corresponding cross on image intensifier be presented as $L_{ij}$, then $$\bar{r} = \frac{h}{H} = \frac{h'}{H+d}, \text{ so } H = \frac{h'}{\bar{r}} - d, \text{ where } \bar{r} = ave\left(\frac{l_{ij}}{L_{ij} - l_{ij}}\right).$$

$$\text{Hence, } h = \frac{H}{H+d}h', \text{ or } h' = \frac{H+d}{H}h.$$

The invention claimed is:

1. A method of operating a targeting system, comprising: providing an adjustable optical assembly including a targeting marker in a path of a penetrating beam of a radiation source, the targeting marker being at least partially opaque to a penetrating beam emitted by the radiation source, and the targeting marker indicating a targeting point on a target axis, the optical assembly further including a sensible targeting beam device that is capable of providing a sensible targeting beam coaxial and coincident with the target axis; providing a first alignment target indicating a first alignment point at a first location in the path of the penetrating beam, the first alignment target being at least partially opaque to the penetrating beam; providing the sensible targeting beam coaxial and coincident with the target axis; adjusting the optical assembly so the sensible targeting beam impinges the first alignment point at the first location, and so an image provided by the receiver indicates the targeting point coincides with the first alignment point at the first location; recording information corresponding to a position of the target axis as a first alignment position; providing a second alignment target indicating a second alignment point at a second location in the path of the penetrating beam, the second alignment target being at least partially opaque to the penetrating beam; adjusting the optical assembly so the sensible targeting beam impinges the second alignment point at the second location, and so an image provided by the receiver indicates the targeting point coincides with the second alignment point at the second location; and recording information corresponding to a position of the target axis as a second alignment position.

2. The method of claim 1, wherein the sensible targeting beam is a laser beam.

3. The method of claim 1, wherein the penetrating beam is an x-ray beam.

4. The method of claim 1, wherein the targeting marker includes a first wire, and includes a second wire substantially perpendicular to the first wire.

5. The method of claim 1, wherein adjusting the optical assembly so the image provided by the receiver indicates the targeting point coincides with any one of the alignment points includes translating at least a part of the optical assembly.

6. The method of claim 1, wherein adjusting the optical assembly so the receiver indicates the targeting point coincides with any one of the alignment points includes rotating at least a part of the optical assembly.

7. The method of claim 1, wherein adjusting the optical assembly so the sensible targeting beam impinges any one of the alignment points includes rotating at least a part of the optical assembly.

8. The method of claim 1, wherein adjusting the optical assembly so the sensible targeting beam impinges any one of the alignment points includes translating at least a part of the optical assembly.

9. The method of claim 1, wherein the sensible targeting beam device includes a laser beam positioned on a second axis and a mirror positioned on the target axis and the second axis.

10. The method of claim 9, wherein the mirror is at least partially translucent to the penetrating beam.

11. The method of claim 1, wherein the targeting point is on a rotational axis of the optical assembly.

12. The method of claim 1, wherein the targeting point is on a translational axis of the optical assembly.

13. The method of claim 1, further comprising determining a center of emanation of the penetrating beam using at least part of the recorded first alignment position and at least part of the recorded second alignment position.

14. A method of operating a targeting system, comprising: providing an adjustable optical assembly including a targeting marker in a path of a penetrating beam of a source, the targeting marker being at least partially opaque to a penetrating beam emitted by the source, and the targeting marker indicating a targeting point on a target axis, the optical assembly further including a sensible targeting beam device that is capable of providing a sensible targeting beam coaxial and coincident with the target axis; providing a alignment target indicating a alignment point at a first location in the path of the penetrating beam, the alignment target being at least partially opaque to the penetrating beam; providing the sensible targeting beam coaxial and coincident with the target axis; adjusting the optical assembly so the sensible targeting beam impinges the alignment point at the first location, and so an image provided by the receiver indicates the targeting point coincides with the alignment point at the first location; recording information corresponding to a position of the target axis as a first alignment position; moving the alignment target to a second location in the path of the penetrating beam; adjusting the optical assembly so the targeting beam impinges the alignment point at the second location, and so an image provided by the receiver indicates the targeting point coincides with the alignment point at the second location; and recording information corresponding to a position of the target axis as a second alignment position.

15. The method of claim 14, wherein the sensible targeting beam is a laser beam.

16. The method of claim 14, wherein the penetrating beam is an x-ray beam.

17. The method of claim 14, wherein the targeting marker includes a first wire-like element, at least partially opaque to the penetrating beam, and includes a second similar wire-like element substantially perpendicular to the first wire-like element.

18. The method of claim 14, wherein adjusting the optical assembly so the image provided by the receiver indicates the targeting point coincides with the alignment point includes translating at least a part of the targeting assembly.

19. The method of claim 14, wherein adjusting the optical assembly so the receiver indicates the targeting point coincides with the alignment point includes rotating at least a part of the optical assembly.

20. The method of claim 14, wherein adjusting the optical assembly so the sensible targeting beam impinges the alignment point includes rotating at least a part of the optical assembly.

21. The method of claim 14, wherein adjusting the optical assembly so the sensible targeting beam impinges the alignment point includes translating at least a part of the optical assembly.

22. The method of claim 14, wherein the sensible targeting beam device includes a laser beam positioned on a second axis and a mirror positioned on the target axis and the second axis.

23. The method of claim 22, wherein the mirror is at least partially translucent to the penetrating beam.

24. The method of claim 14, wherein the targeting point is on a rotational axis of the optical assembly.

25. The method of claim 14, wherein the targeting point is on a translational axis of the optical assembly.

26. The method of claim 14, further comprising determining a center of emanation of the penetrating beam using at least part of the recorded, first alignment position and at least part of the recorded second alignment position.

27. A targeting system, comprising: an optical assembly including a targeting marker in a path of a penetrating beam provided by a source, the targeting marker being at least partially opaque to a penetrating beam emitted by the source, and the targeting marker indicating a targeting point on a target axis, the optical assembly further including a targeting beam device capable of providing a sensible targeting beam coaxial and coincident with the target axis; a first alignment target indicating an alignment point located in the path of the penetrating beam, the first alignment target being at least partially opaque to the penetrating beam; and a position recorder capable of recording information corresponding to at least two alignment positions of the target axis.

28. The system of claim 27, further comprising a second alignment target indicating a second alignment point located in the path of the penetrating beam, the second alignment target being at least partially opaque to the penetrating beam.

29. The system of claim 27, wherein the sensible targeting beam is a laser beam.

30. The system of claim 27, wherein the penetrating beam is an x-ray beam.

31. The system of claim 27, wherein the targeting marker includes a first wire-like element, at least partially opaque to the penetrating beam, and includes a second similar wire-like element substantially perpendicular to the first wire-like element.

32. The system of claim 27, wherein the position recorder includes a computer and software for running on the computer.

33. The system of claim 27, wherein the sensible targeting beam device includes a laser beam positioned on a second axis and a mirror positioned on the target axis and the second axis.

34. The system of claim 33, wherein the mirror is at least partially translucent to the penetrating beam.

35. The system of claim 27, wherein the targeting point is on a rotational axis of the optical assembly.

36. The system of claim 27, wherein the targeting point is on a translational axis of the optical assembly.

* * * * *